United States Patent
Christensen et al.

(10) Patent No.: US 7,229,554 B2
(45) Date of Patent: Jun. 12, 2007

(54) PURIFICATION PROCESS COMPRISING MICROFILTRATION AT ELEVATED TEMPERATURES

(75) Inventors: Lars Hojlund Christensen, Vaerlose (DK); Torben Kjaersgaard Nielsen, Roskilde (DK)

(73) Assignee: Novo Nordisk A/S, Bagsvaerd (DK)

(*) Notice: Subject to any disclaimer, the term of this patent is extended or adjusted under 35 U.S.C. 154(b) by 79 days.

(21) Appl. No.: 10/671,064

(22) Filed: Sep. 25, 2003

(65) Prior Publication Data

US 2004/0164023 A1 Aug. 26, 2004

Related U.S. Application Data

(60) Provisional application No. 60/413,729, filed on Sep. 26, 2002.

(30) Foreign Application Priority Data

Sep. 25, 2002 (DK) ............... 2002 01422

(51) Int. Cl.
*B01D 61/00* (2006.01)
*B01D 63/00* (2006.01)

(52) U.S. Cl. ............ 210/651; 210/650; 210/175; 435/200; 435/209; 435/289; 426/61

(58) Field of Classification Search ........ 210/650, 210/651, 652, 630, 175, 649; 435/200, 209, 435/289.1, 85.2, 69.7, 235.1; 530/350; 426/61, 426/64, 18
See application file for complete search history.

(56) References Cited

U.S. PATENT DOCUMENTS

| | | | | |
|---|---|---|---|---|
| 4,724,080 A | | 2/1988 | Dau et al. .............. 210/651 |
| 5,143,630 A | * | 9/1992 | Rolchigo ............... 210/780 |
| 5,202,239 A | * | 4/1993 | Tarnowski et al. ....... 435/69.7 |
| 5,262,053 A | | 11/1993 | Meier .................. 210/636 |
| 5,322,930 A | * | 6/1994 | Tarnowski et al. ....... 530/350 |
| 5,417,970 A | * | 5/1995 | Roskam et al. .......... 424/85.2 |
| 5,453,200 A | * | 9/1995 | Weiss et al. ........... 210/639 |
| 5,508,196 A | | 4/1996 | Mannweiler et al. ..... 435/289.1 |
| 5,712,142 A | * | 1/1998 | Adney et al. ........... 435/209 |
| 5,879,557 A | | 3/1999 | Strohm et al. .......... 210/636 |
| 5,933,889 A | * | 8/1999 | Eekhoff ................ 5/611 |
| 6,207,437 B1 | * | 3/2001 | Gros et al. ............ 435/220 |
| 6,207,806 B1 | * | 3/2001 | Brierley et al. ........ 530/416 |
| 6,582,606 B2 | * | 6/2003 | Laustsen et al. ........ 210/639 |
| 6,812,000 B2 | * | 11/2004 | Wilkins et al. ......... 435/41 |
| 6,814,861 B2 | * | 11/2004 | Husain et al. .......... 210/257.2 |
| 7,125,706 B2 | * | 10/2006 | Zhang et al. ........... 435/235.1 |

FOREIGN PATENT DOCUMENTS

| | | |
|---|---|---|
| DE | 42 34 392 A1 | 4/1994 |
| GB | 2 155 356 A | 9/1985 |
| WO | 00/45938 | 8/2000 |
| WO | WO 01/87468 A1 | 11/2001 |

OTHER PUBLICATIONS

P. W. Atkins. Physical Chemistry. Oxford University Press. pp. 934-947 (1986).
Bailey. et al: Biochemical Engineering Fundamentals. Second Edition. pp. 129-148.
International Search Report dated Jan. 21, 2004.

* cited by examiner

*Primary Examiner*—Ana M. Fortuna
(74) *Attorney, Agent, or Firm*—Richard W. Bork; Reza Green

(57) ABSTRACT

Process for microfiltration at elevated temperature.

31 Claims, 2 Drawing Sheets

PURIFICATION PROCESS COMPRISING MICROFILTRATION AT ELEVATED TEMPERATURES

CROSS REFERENCE TO RELATED APPLICATIONS:

This application claims priority under 35 U.S.C. 119 of Danish Application No. PA 2002 01422 filed Sep. 25, 2002 and of U.S. Provisional Application No. 60/413,729 filed Sep. 26, 2002, the contents of which are fully incorporated herein by reference.

FIELD OF THE INVENTION

The present invention relates to a process for purification of fermentation-derived products. More specifically the processes of the invention pertain to improved microfiltration processes comprising elevated temperatures.

BACKGROUND OF THE INVENTION

The conventional method for recovering fermentation-derived products, such as proteins and antibiotics, from the complex fermentation broth matrix is a series of clarification steps to remove insoluble material and one or more steps employing liquid chromatography. Liquid chromatography comprises the application of the product holding fluid onto a solid chromatographic matrix under conditions where the fermentation-derived product binds to the chromatographic matrix while the bulk of impurities pass through the chromatographic column. After a washing phase the bound product is eluted from the column.

This method has several drawbacks. First, chromatography is an expensive method for recovery of fermentation derived products. Second, chromatography is not well suited for continuous processes which are often used in the industrial manufacture of fermentation-derived products. Third, chromatographic column operation is not robust towards normal fermentation-derived impurities such as remnant cells and cellular debris, antifoam, host cells proteins and proteases. Often many sequential steps are needed for a chromatographic recovery, including upstream centrifugation and filtration steps and several chromatographic steps each targetting a certain group of impurities.

Microfiltration has also been used for the purification steps following fermentation. Usually the fermentation broth is cooled in order to attenuate the degradation of the product as well as to inhibit contaminating microorganisms. The ensuing microfiltration is then performed at temperatures of 0° C. to 30° C. to have a compromise between product degradation and performance of the microfiltration. One exception is WO01/87468 which discloses a microfilmtration process of a fermentation-derived product comprising adding activated carbon to a solution of the fermentation-derived product prior to or during the microfiltration process at a microfiltration process temperature of from 25° C. to 65° C.

Generally however, it is a teaching within the field of biotechnology that fermentation-derived products such as protein and antibiotics should be kept in solution at as low temperatures as possible in order to prevent microbial, enzymatic or chemical degradation of the product (Biochemical Engineering Fundamentals, J. E. Bailey, D. F. Ollis, McGraw-Hill Inc., 1986 and Physical Chemistry, P. W. Atkins, Oxford Univ. Press, 1986).

Surprisingly, the present inventors have found that a method for the industrial manufacture of fermentation-derived products which utilizes a microfiltration step performed at elevated temperatures, enables continuous manufacturing and better separation of product and impurities while requiring a reduced number of manufacturing steps.

SUMMARY OF THE INVENTION

It is an object of the present invention to provide a process for purifying a fermentation-derived product, said process comprising the steps:
  a) microfiltration of a fermentation broth containing the fermentation-derived product at a microfiltration temperature within the range from 66° C. to 90° C.;
  b) isolation of the final product.

It is a further object of the invention to provide a process for purifying a fermentation-derived product, said process comprising the steps:
  a) microfiltration of a fermentation broth containing the fermentation-derived product at a microfiltration temperature within the range from 66° C. to 90° C., wherein the microfiltration is performed in the absence of activated carbon;
  b) isolation of the final product.

In one embodiment the process may utilize a microfiltration temperature within the range from 70° C. to 90° C. In another embodiment the process may utilize a microfiltration temperature within the range from 70° C. to 80° C.

It is another object of the present invention to provide a process wherein the microfiltration is performed as a cross flow microfiltration.

It is another object of the present invention to provide a process wherein the microfiltration process is performed with a vibrating microfiltration membrane.

It is another object of the present invention to provide a process wherein the microfiltration process is performed with backshock.

DESCRIPTION OF THE INVENTION

Figure 1:
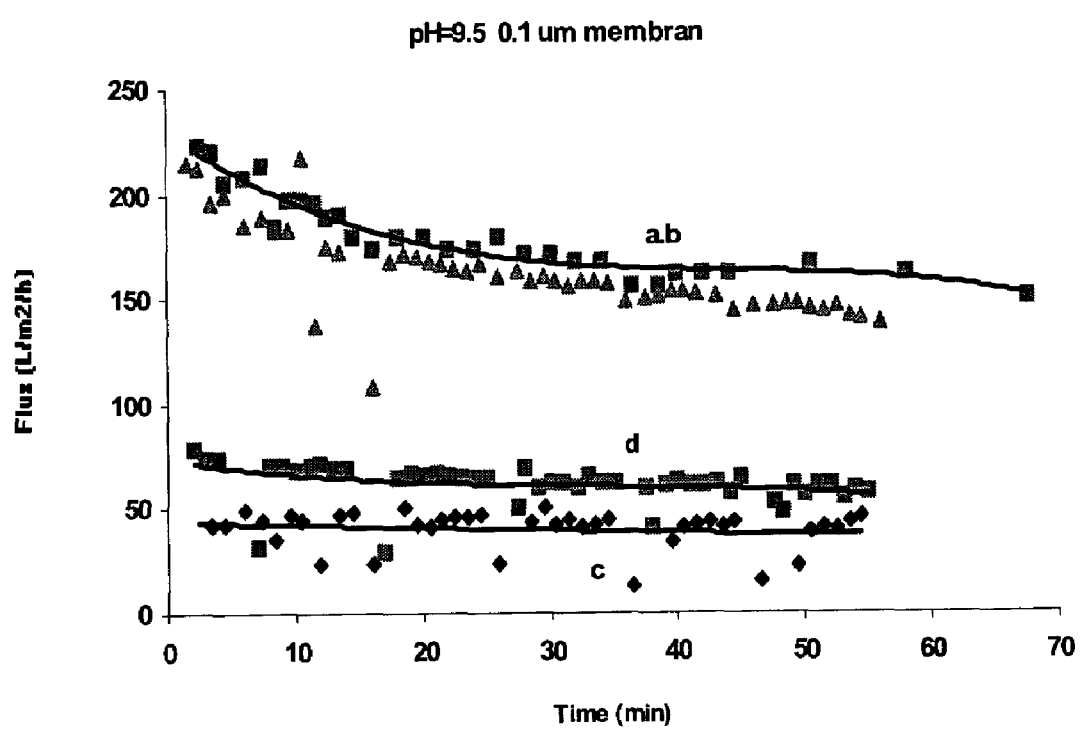
FIG. 1. Calculated flux of permeate through the ceramic membrane as a function of time shown for different filtration temperatures: curve a,b: 77-80° C., curve c: 32-35° C. and curve d: 32-35° C. using cell free broth which had been heated to 80-90° C. and cooled to 34° C. prior to start of the filtration experiment (marked "preheated"). The reservoir vessel was pressurized to 0.9 bar overpressure, the broth was recirculated at a speed of 200 L/hour and back-shock was performed every 30 seconds for curve a and b, whereas a backshock frequency of 60 seconds was used for curve c and d.

Microfiltration membranes may be formed from a variety of materials such as natural polymers, synthetic polymers, ceramics and metals. Preferred microfiltration membranes are ceramic membranes which may be formed by fibres of silicon carbide, silicon nitride, aluminosilicate, zirconium, mixtures thereof and which may optionally be carbon-coated (see e.g. WO 00/45938). Preferred metal microfiltration membranes are zirconium membranes.

The nominal pore size of MF membranes are typically in the range from 0.01 μm to 10 μm, preferably from 0.05 μm to 7.5 μm and more preferable from 0.1 μm to 2 μm. In order to prevent polarization of the membrane, the MF process is typically carried out using cross flow filtration where the broth also flows along the membrane surface, e.g. such as used by classical cross flow filtration. Other ways to obtain the same result are to move the membrane, as used in e.g. vibrating membrane filtration, or to apply backshock or backflush where the flow through the membrane is intermittently reversed.

One aspect of the present invention is a process for purifying a fermentation-derived product, said process comprising the steps:
a) microfiltration of a fermentation broth containing the fermentation-derived product at a microfiltration temperature within the range from 66° C. to 90° C.;
b) isolation of the final product.

The final product may be identical to the fermentation-derived product or it may be a chemically modified equivalent of the fermentation-derived product. For instance, the final product from a fermentation derived product which is a protein may be a truncated protein, a fused protein, a derivatized protein or a combination of these. Indeed proteins are often expressed as precursors in the host cells, said precursors being chemically modified during the downstream process steps used to purify and to isolate the final product. The precursor typically is the product protein with an amino acid extension which increases the yield in the fermentation process or which facilitates purification steps such as affinity chromatography, e.g. IMAC purification of his-tagged proteins. Likewise, organic molecules such as antibiotics may be produced by the host cells as a fermentation-derived product which has to be chemically modified to obtain the final product.

The term "analogue" as used herein referring to a protein or a peptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. Two different and simple systems are often used to describe analogues: For example $Arg^{34}$-GLP-1(7-37) or K34R-GLP-1(7-37) designates a GLP-1 analogue wherein the naturally occuring lysine at position 34 has been substituted with arginine (standard single letter abbreviation for amino acids used according to IU-PAC-IUB nomenclature).

Fermentation broth is defined as fermentation medium containing the fermentation-derived product. The fermentation broth may also contain host cells, it may be substantially free of host cells or it may be completely free of host cells. Thus, the fermentation broth may be a solution but usually it is a more or less clarified broth where only minor amounts of insoluble materials such as cells, cellular debris and precipitated protein and salts are present. Preferably the fermentation broth contains less than 10 g/L, less than 2 g/L, less than 0.5 g/L or less than 0.1 g/L of insoluble material as determined gravimetrically by filtration through a 0.22 μm filter and subsequently drying it at 105° C. for 20 hours. A clarified fermentation broth is a fermentation broth containing less than 0.5 g/L insoluble material as determined by above gravimetrical method.

Another aspect of the present invention is a process for purifying a fermentation-derived product, said process comprising the steps:
a) microfiltration of a fermentation broth containing the fermentation-derived product at a microfiltration temperature within the range from 66° C. to 90° C., wherein the microfiltration is performed in the absence of activated carbon;
b) isolation of the final product.

In one embodiment the microfiltration temperature is within the range from 70° C. to 90° C.

In another embodiment the microfiltration temperature is within the range from 70° C. to 80° C. The microfiltration process of the present invention is preferably carried out using equipment and operating mode which prevent or reduce the build-up of a polarizing layer at the membrane. The polarizing layer causes the flux across the membrane to decline and it may also reduce the transmission, i.e. the product concentration in the permeate divided by the product concentration in the retentate. Build-up of a polarizing layer may be reduced or prevented by introducing fluid motion along the microfiltration membrane.

In another embodiment the microfiltration is performed as a cross flow microfiltration.

In another embodiment the microfiltration process is performed with a vibrating microfiltration membrane.

In another embodiment the microfiltration process is performed with backshock, i.e. a temporary reversal of the flow through the microfiltration membrane.

In another embodiment the microfiltration process is performed using a microfiltration membrane formed from a material selected from the group consisting of natural polymers, synthetic polymers, ceramics, metals and mixtures thereof.

In another embodiment the microfiltration process is performed using a polysulphone membrane.

In another embodiment the microfiltration process is performed as a batch process.

In another embodiment the microfiltration process is performed using a fermentation broth with a pH from pH 3 to pH 10, from pH 5 to pH 10, from pH 4 to pH 9, from pH 5 to pH 8, such as pH 6 or pH 7.

In another embodiment the microfiltration process is performed as a continuous process.

In another embodiment the microfiltration process is followed by an ultrafiltration process.

In another embodiment the cut-off value of the UF membrane is lower than four times the molecular weight of the fermentation-derived product, preferably lower than twice the molecular weight of the fermentation-derived product and most preferably lower than the molecular weight of the fermentation-derived product.

In another embodiment of the invention the microfiltration process is followed by an ultrafiltration process, said ultrafiltration being performed at a temperature in the range from 0° C. to about 25° C.

In another embodiment the microfiltration process is followed by at least one chromatographic step or at least one precipitation step.

In another embodiment the fermentation-derived product is at temperatures higher than 60° C. for less than 30 minutes, preferably for less than 15 minutes, even more preferable for less than 10 minutes, and most preferable for less than 5 minutes.

In another embodiment the fermentation-derived product is a protein.

In another embodiment the fermentation-derived product is a microbially derived protein.

In another embodiment the host cell producing said protein is selected from the group consisting of *E. coli, Saccharomyces, Pichia, Candida* and *Kluyveromyces*.

In another embodiment said protein is a pharmaceutical protein or a precursor thereof.

In another embodiment the fermentation-derived product is a protein with a molar weight of less than 25000 Dalton, less than 10000 Dalton, less than 7000 Dalton, or less than 4000 Dalton.

In another embodiment the fermentation-derived product is a pharmaceutical protein which is selected from the group consisting of GLP-1, GLP-2, glucagon, TFF peptides, interleukins, insulin, albumin, precursors thereof and analogs of any of the foregoing.

In another embodiment said protein is selected from the group consisting of human insulin, a human insulin precursor, a human insulin analog, a human insulin analog precursor and $Arg^{34}$-GLP-1(7-37).

In another embodiment of the invention the fermentation-derived product is a GLP-1 peptide selected from the group consisting of $Arg^{34}$-GLP-1(7-37), $Gly^8$-GLP-1(7-36)-amide, $Gly^8$-1(7-37), $Val^8$-GLP-1(7-36)-amide, $Val^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37), $Val^8Trp^{19}Glu^{22}$-GLP-1(7-37), $Val^8Glu^{22}Val^{25}$-GLP-1(7-37), $Val^8Tyr^{16}Glu^{22}$-GLP-1(7-37), $Val^8Trp^{16}Glu^{22}$-GLP-1(7-37), $Val^8Leu^{16}Glu^{22}$-GLP-1(7-37), $Val^8Tyr^{18}Glu^{22}$-GLP-1(7-37), $Val^8Glu^{22}His^{37}$-GLP-1(7-37), $Val^8Glu^{22}Ile^{33}$-GLP-1(7-37), $Val^8Trp^{16}Glu^{22}Val^{25}Ile^{33}$-GLP-1(7-37), $Val^8Trp^{16}Glu^{22}Ile^{33}$-GLP-1(7-37), $Val^8Glu^{22}Val^{25}Ile^{33}$-GLP-1(7-37), $Val^8Trp^{16}Glu^{22}Val^{25}$-GLP-1(7-37) and analogs thereof.

In another embodiment of the invention the fermentation-derived product is a GLP-2 peptide selected from the list consisting of: K30R-GLP-2(1-33); S5K-GLP-2(1-33); S7K-GLP-2(1-33); D8K-GLP-2(1-33); E9K-GLP-2(1-33); M10K-GLP-2(1-33); N11K-GLP-2(1-33); T12K-GLP-2(1-33); I13K-GLP-2(1-33); L14K-GLP-2(1-33); D15K-GLP-2(1-33); N16K-GLP-2(1-33); L17K-GLP-2(1-33); A18K-GLP-2(1-33); D21K-GLP-2(1-33); N24K-GLP-2(1-33); Q28K-GLP-2(1-33); S5K/K30R-GLP-2(1-33); S7K/K30R-GLP-2(1-33); D8K/K30R-GLP-2(1-33); E9K/K30R-GLP-2(1-33); M10K/K30R-GLP-2(1-33); N11K/K30R-GLP-2(1-33); T12K/K30R-GLP-2(1-33); I13K/K30R-GLP-2(1-33); L14K/K30R-GLP-2(1-33); D 15K/K30R-GLP-2(1-33); N16K/K30R-GLP-2(1-33); L17K/K30R-GLP-2(1-33); A18K/K30R-GLP-2(1-33); d21K/K30R-GLP-2(1-33); N24K/K30R-GLP-2(1-33); Q28K/K30R-GLP-2(1-33); K30R/D33K-GLP-2(1-33); D3E/K30R/D33E-GLP-2(1-33); D3E/S5K/K30R/D33E-GLP-2(1-33); D3E/S7K/K30R/D33E-GLP-2(1-33); D3E/D8K/K30R/D33E-GLP-2(1-33); D3E/E9K/K30R/D33E-GLP-2(1-33); D3E/M10K/K30R/D33E-GLP-2(1-33); D3E/N11K/K30R/D33E-GLP-2(1-33); D3E/T12K/K30R/D33E-GLP-2(1-33); D3E/I13K/K30R/D33E-GLP-2(1-33); D3E/L14K/K30R/D33E-GLP-2(1-33); D3E/D15K/K30R/D33E-GLP-2(1-33); D3E/N16K/K30R/D33E-GLP-2(1-33); D3E/L17K/K30R/D33E-GLP-2(1-33); D3E/A18K/K30R/D33E-GLP-2(1-33); D3E/D21K/K30R/D33E-GLP-2(1-33); D3E/N24K/K30R/D33E-GLP-2(1-33); D3E/Q28K/K30R/D33E-GLP-2(1-33); and precursors thereof. In above nomenclature single amino acid abbreviations are used in accordance with IUPAC-IUB nomenclature, and for example the analog D3E-GLP-2(1-33) means the GLP-2 peptide resulting from substituting the naturally occurring amino acid D (aspartic acid) in position 3 with an E (glutamic acid).

In another embodiment of the invention the fermentation-derived product is a peptide selected from the group consisting of exendin-3, exendin-4, analogs thereof such as ZP-10 (HGEGTFTSDLSKQMEEEAVR-LFIEWLKNGGPSSGAPPSKKKKKK-NH2) and precursors of any of the foregoing.

EXAMPLES

Example 1

Fermentation broth from a continuous fermentation producing $Arg^{34}$-GLP-1(7-37) was adjusted to pH=9.5 through addition of NaOH. The pH value of 9.5 was maintained for 10 minutes. Subsequently, the alkaline broth was centrifuged at 3-4000 g for 10 minutes in order to remove the yeast strain used for the heterologous, extracellular expression. Each test solution was spiked with a second antifoam agent besides the one already added during the fermentation. This was done in order to assure a high content of antifoam agent in the treated broth.

Filtration

The cell free medium was heated to approx. 75-80° C. within 3-5 minutes by blowing steam through a jacketed, stirred vessel. A temperature of 80-90° C. was maintained for 2-5 minutes. The heated cell-free broth was then transferred to the filtration system including a preheated, jacketed reservoir tank pressurized to 0.9 bar overpressure. A temperature of 77-80° C. was maintained in the reservoir tank throughout the filtration process. Recirculation of cell-free broth across a ceramic membrane (50 square centimeters, 0.1 μzirconium) was carried out at a rate of approximately 200 liter/hour. Pneumatic backshock of permeate was performed every 30-60 seconds using a backshock volume of approximately approx. 3 mL.

Filtration of cell free broth (pH=9.5) at 32-35° C. served as a reference/base line for the evaluation of the filtration performance at a setpoint of 80° C. When carrying out filtration at a setpoint of 34° C. two types of cell-free broth was applied: a) alkaline (pH=9.5) cell free broth with no pre-treatment and b) alkaline (pH=9.5) cell-free broth which had been heated to 80-90° C. for 6 minutes followed by cooling to 34° C. prior to initiation of the filtration step (referred to as "preheated").

Example 2

Flux of Permeate

The net flux of permeate through the membrane was measured by collecting the permeate leaving the filtration module. Placing the container for collecting permeate on a precision balance allowed for calculation of the net flux. Compensation for the amount of permeate retrieved as sample material was included in the calculations of the net flux. Filtration and re-circulation of broth was maintained for 60-75 minutes. The calculated flux of permeate through the membrane in units of $L/m^2/h$ are shown in FIG. 1. The significantly higher net flux of permeate through the membrane when operated at 77-80° C. as compared to 32-35° C. is demonstrated in FIG. 1. The impact of heating the cell-free broth to 80–90° C. for a short period of time prior to filtration at 32–35° C. had only minor impact on the achieved net flux.

Example 3

Transmission

Figure 2:
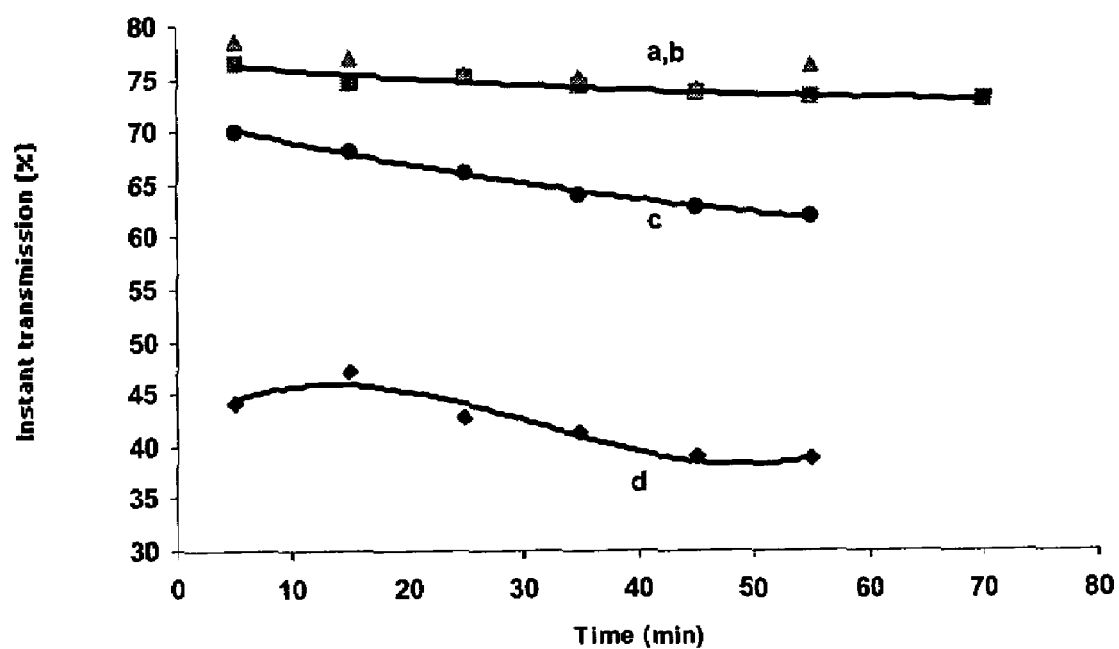
FIG. 2. Transmission of $Arg^{34}$-GLP-1-(7-37) as a function of filtration time shown for different filtration temperatures. Curve a) and b) filtration at 77-80° C., curve c) filtration at 32-35° C. using broth preheated to app. 80-90° C. for 10 minutes ("preheated") and curve d) filtration at 32-35° C.

During the filtration process samples of both retentate and permeate were retrieved every 5–10 minutes. These sets of samples were subsequently analyzed by HPLC for their concentration of $Arg^{34}$-GLP-1(7-37). From these numbers the instantaneous transmission was calculated as a function of filtration time. The transmission at time (t) was calculated by dividing the concentration of product in the permeate at time (t) with the concentration found in the retentatet at time (t). The results of these calculations are shown graphically in FIG. 2.

Carrying out the filtration at 77–80° C. instead of 32–35° C. results in close to a doubling of the transmission of product through the membrane. However, heating the cell-free broth to 80–90° C. for a short period of time (6 minutes) also increases the transmission of $Arg^{34}$-GLP-1(7-37) through the membrane albeit to a minor extent than observed when maintaining a high temperature throughout the filtration process.

Example 4

Removal of Host Cell Protein (HCP)

The retention of Host cell protein and high molecular weight components by the membrane was quantified using immuno-techniques for the measurement of yeast cell derived products containing an epitope. The quantification of Host cell protein relied on the usage of antibodies raised against the yeast strain used for heterologous expression of product different from $Arg^{34}$-GLP-1(7-37).

The reduction factors (RF) reflecting the decrease in host cell protein after 5 minutes of filtrateion are listed in table 1. It was calculated by dividing the immological response obtained in the retentate with the result obtained for the permeate. Specific immunological responses are listed in column 2 and 3 for the retentate and permeate, respectively.

TABLE 1

Immunological responses for Host Cell Protein when carrying out the filtration at different temperatures using cell-free broth adjusted to a pH of 9.5. The reduction factor (RF) expresses the ratio between the response obtained for the retentate divided with the response obtained for the permeate both measured after 5 minutes of filtration.

| Condition | Response ppm (Retentate) | Response ppm (Permeate) | RF |
|---|---|---|---|
| 77–80° C. (pH = 9.5) | 11058 | 720 | 15.4 |
| 77–80° C. (pH = 9.5) | 16448 | 1000 | 16.4 |
| 32–35° C. | 21575 | 5903 | 3.7 |
| 32–35° C. (preheated) | 18188 | 5223 | 3.5 |

The data in table 1 show that removal of Host cell protein as reflected by the reduction factors (RF) is superior for filtration carried out at 77–80° C. as compared to filtration performed at only 32–35° C. Even preheating of the cell-free culture broth to approximately 80-90° C. for 6 minutes does not improve the removal of host cell protein when the broth temperature is maintained at 32–35° C. during the filtration process.

The experiment carried out at 77–80° C. with cell-free broth of pH=9.5 was repeated but this time using cell-free fermentation broth of pH=5.5. The reduction factor measured for this broth is shown in table 2. Reduction of the host cell protein content by a factor of nearly 30 is considered very efficient when compared to the numbers obtained at pH=9.5 (see table 1). Consequently, pH of the broth during filtration at high temperature does seemingly not impede the efficient removal of host cell protein during filtration with the ceramic module.

TABLE 2

Immunological responses for host cell protein of the retentate and permeate when the filtration was performed at 77–80° C. but using a broth pH of 5.5. Responses measured after 5 minutes of filtration.

| Condition | Response ppm (Retentate) | Response ppm (Permeate) | RF |
|---|---|---|---|
| 80° C. (pH = 5.5) | 19050 | 656 | 29 |

Example 5

Removal of antifoam agents

The fermentation broth was produced using an antifoam agent in order to control foaming of the microbial culture. After adjustment of broth pH to 9.5 and removal of the cells by centrifugation the broth was spiked with a second antifoam agent (modified polyalcoxyether) leading to total antifoam levels in the range of 1000-1210 ppm.

Samples of the spiked broth were retrieved prior to the start of the filtration. A second series of samples were retrieved from the pool of permeate collected during the entire filtration experiment. Both series of samples were analyzed for their content of antifoam. Quantification of antifoam agent concentration was carried out using a solid phase extraction followed by GPC using refractive index detection. The results of these analyses are shown in table 3.

TABLE 3

Concentration of antifoam expressed in units of part per million in the cell free broth before start of filtration and in the pool of permeate collected during the entire experiment.

| | Antifoam agent 1 | | Antifoam agent 2 | |
|---|---|---|---|---|
| Condition | Before | Pooled permeate | Before | Pooled permeate |
| 77–80° C. | 550 ppm | <10 ppm | 660 ppm | <10 ppm |
| 32–35° C. | 550 ppm | 280 ppm | 460 ppm | 95 ppm |

Data presented in table 3 demonstrate that filtration at 80° C. is superior to filtration at 32–35° C. with regard to the removal of both antifoam agent 1 and antifoam agent 2 from the cell free fermentation broth.

Example 6

$Arg^{34}GLP-1_{(7-37)}$ was expressed in yeast (*S. cerevisiae*) by conventional recombinant DNA technology, e.g. as described in WO 98/08871. Fermentation broth from a continuous fermentation producing $Arg^{34}$-GLP1(7-37) was adjusted to pH=9.5 by addition of NaOH. The pH value of 9.5 was maintained for 10 minutes. The alkaline broth was then centrifuged at 3-4000 g for 10 minutes in order to remove the yeast host strain.

Filtration

The cell free medium was heated to 75-80° C. within 3-5 minutes by blowing steam through the jacket of a stirred vessel. A temperature of 80-90° C. was maintained for 2-5 minutes. The heated cell-free broth was then transferred to a filtration system and maintained at 77-80° C. throughout the filtration process. Recirculation of cell-free broth across a ceramic membrane (50 square centimetres, 0.1 μm zirconium) was carried out at a flow rate of 200 liter/hour. Pneumatic back-shock of permeate was carried out every 30-60 seconds using a back-shock volume of approximately 3 mL.

Concentration

The permeate from the filtration step was pH adjusted to 7.0 using a strong acid and transferred to an ultrafiltration device containing a 5K ultrafiltration membrane made of either polysulfone (Millipore cat. No. PxB005A50) or regenerated cellulose (Millipore cat. No. PXC005C50). Concentration of the Arg$^{34}$-GLP1(7-37) was carried out at an average trans-membrane pressure of 20-40 psi allowing for a flow of permeate in the range of 20-50 L/square meter/hour. The ultrafiltration step was carried out at temperatures below 10° C. The relative concentration of retained product and leakage of product (in the permeate) as a function of time is shown in table 4 and 5 for two different types of membranes.

TABLE 4

Relative concentrations of Arg$^{34}$-GLP1(7–37) in the retentate and the permeate as a function of time when using an UF membrane of polysulfone with a cut-off value of 5K.

| Time | Relative concentration in the Retentate | Relative concentration in permeate. |
|---|---|---|
| 5 min | 1 | 0.002 |
| 120 min | 1.3 | 0.080 |
| 180 min | 1.8 | 0.090 |
| 245 min | 3.5 | 0.117 |

TABLE 5

Relative concentrations of Arg$^{34}$-GLP1(7–37) in the retentate and the permeate as a function of time when using an UF membrane of regenerated cellulose with a cut-off value of 5K.

| Time | Relative concentration in the Retentate | Relative concentration in permeate. |
|---|---|---|
| 5 min | 1 | 0.002 |
| 120 min | 1.6 | 0.005 |
| 180 min | 2.6 | 0.009 |
| 245 min | 5.0 | 0.021 |

The invention claimed is:

1. A process for purifying a fermentation-derived protein with a molar weight of less than 25000 Dalton, said process comprising microfiltration of a fermentation broth containing the protein at a microfiltration temperature within the range from 66° C. to 90° C. wherein said protein passes through the microfiltration membrane.

2. The process according to claim 1, wherein said microfiltration is performed in the absence of activated carbon.

3. The process according to claim 1, wherein the microfiltration temperature is within the range from 70° C. to 90° C.

4. The process according to claim 1, wherein the microfiltration temperature is within the range from 70° C. to 80° C.

5. The process according to claim 1, wherein the microfiltration is performed as a cross flow microfiltration.

6. The process according to claim 5, wherein the microfiltration process is performed with a vibrating microfiltration membrane.

7. The process according to claim 5, wherein the microfiltration process is performed with backshock.

8. The process according to claim 1, wherein the microfiltration process is performed using a microfiltration membrane formed from a material selected from the group consisting of natural polymers, synthetic polymers, ceramics, metals and mixtures thereof.

9. The process according to claim 1, wherein the microfiltration process is performed using a polysulphone membrane.

10. The process according to claim 1, wherein the microfiltration process is performed as a batch process.

11. The process according to claim 1, wherein the microfiltration process is performed as a continuous process.

12. The process according to claim 1, wherein the microfiltration process is followed by an ultrafiltration process.

13. The process according to claim 12, wherein the cut-off value of the ultrafiltration membrane is lower than four times the molecular weight of the fermentation-derived protein.

14. The process according to claim 12, wherein the cut-off value of the ultrafiltration membrane is lower than twice the molecular weight of the fermentation-derived protein.

15. The process according to claim 12, wherein the cut-off value of the ultrafiltration membrane is lower than the molecular weight of the fermentation-derived product.

16. The process according to claim 1, wherein the microfiltration process is followed by at least one chromatographic step or at least one precipitation step.

17. The process according to claim 1, wherein the protein is at temperatures higher than 66° C. for less than 60 minutes.

18. The process according to claim 1, wherein the protein is at temperatures higher than 66° C. for less than 30 minutes.

19. The process according to claim 1, wherein the protein is at temperatures higher than 66° C. for less than 15 minutes.

20. The process according to claim 1, wherein the protein is at temperatures higher than 66° C. for less than 10 minutes.

21. The process according to claim 1, wherein the protein is produced by a, host cell selected from the group consisting of *E. coli, Saccharomyces, Pichia, Candida* and *Kluyveromyces*.

22. The process according to claim 1, wherein the protein is a protein with a molar weight of less than 10000 Dalton.

23. The process according to claim 1, wherein the protein is a protein with a molar weight of less than 7000 Dalton.

24. The process according to claim 1, wherein the protein is a protein with a molar weight of less than 4000 Dalton.

25. The process according to claim 1, wherein said protein is selected from the group consisting of glucagon-like peptide 1 (GLP-1), glucagon-like peptide 2 (GLP-2), glucagon, trefoil factor (TFF) peptides, insulin, precursors thereof and analogs of any of the foregoing.

26. The process according to claim 25, wherein said protein is selected from the group consisting of human insulin, a human insulin precursor, a human insulin analog, a human insulin analog precursor, and Arg$^{34}$-GLP-1(7-37).

27. The process according to claim 25, wherein said protein is selected from the group consisting of Arg$^{34}$-GLP-1(7-37), Gly$^8$-GLP-1(7-36)-amide, Gly$^8$-GLP-1(7-37), Val$^8$-GLP-1(7-36)-amide, Val$^8$-GLP-1(7-37), Val$^8$Asp$^{22}$-GLP-1(7-36)-amide, Val$^8$Asp$^{22}$-GLP-1(7-37), Val$^8$Glu$^{22}$-GLP-1(7-36)-amide, Val$^8$Glu$^{22}$-GLP-1(7-37), Val$^8$Lys$^{22}$-GLP-1(7-36)-amide, Val$^8$Lys$^{22}$-GLP-1(7-37), Val$^8$Arg$^{22}$-GLP-1(7-36)-amid; Val$^8$Arg$^{22}$-GLP-1 (7-37), Val$^8$His$^{22}$-GLP-1(7-36)-amide, Val$^8$His$^{22}$-GLP-1(7-37), Val$^8$Trp$^{19}$Glu$^{22}$-GLP-1(7-37), Val$^8$Glu$^{22}$Val$^{25}$-GLP-1(7-37), Val$^8$Tyr$^{16}$Glu$^{22}$-GLP-1(7-37), Val$^8$Trp$^{16}$Glu$^{22}$-GLP-1(7-37), Val$^8$Leu$^{16}$Glu$^{22}$-GLP-1(7-37), Val$^8$Tyr$^{18}$Glu$^{22}$-GLP-1(7-37), Val$^8$Glu$^{22}$His$^{37}$-GLP-1(7-37), Val$^8$Glu$^{22}$Ile$^{33}$-GLP-1(7-37), Val$^8$Trp$^{16}$Glu$^{22}$Val$^{25}$Ile$^{33}$-GLP-1(7-37), Val$^8$Trp$^{16}$Glu$^{22}$Ile$^{33}$-GLP-1(7-37), Val$^8$Glu$^{22}$Val$^{25}$Ile$^{33}$-GLP-1(7-37), Val$^8$Trp$^{16}$Glu$^{22}$Val$^{25}$-GLP-1(7-37) and analogs thereof.

28. The process according to claim 25, wherein said protein is selected from the group consisting of: K30R-GLP-2(1-33); S5K-GLP-2(1-33); S7K-GLP-2(1-33); D8K-GLP-2(1-33); E9K-GLP-2(1-33); M10K-GLP-2(1-33); N11K-GLP-2(1-33); T12K-GLP-2(1-33); I13K-GLP-2(1-33); L14K-GLP-2(1-33); D15K-GLP-2(1-33); N16K-GLP-2(1-33); L17K-GLP-2(1-33); A18K-GLP-2(1-33); D21K-GLP-2(1-33);N24K-GLP-2(1-33); Q28K-GLP-2(1-33); S5K/K30R-GLP-2(1-33); S7K/K30R-GLP-2(1-33); D8K/K30R-GLP-2(1-33); E9K/K30R-GLP-2(1-33); M10K/K30R-GLP-2(1-33); N11K/K30R-GLP-2(1-33); T12K/K30R-GLP-2(1-33); T13K/K30R-GLP-2(1-33); L14K/K30R-GLP-2(1-33); D15K/K30R-GLP-2(1-33); N16K/K30R-GLP-2(1-33); L17K/K30R-GLP-2(1-33); A18K/K30R-GLP-2(1-33); D21K/K30R-GLP-2(1-33); N24K/K30R-GLP-2(1-33); Q28K/K30R-GLP-2(1-33); K30R/D33K-GLP-2(1-33); D3E/K30R/D33E-GLP-2(1-33); D3E/S5K/K30R/D33E-GLP-2(1-33); D3E/S7K/K30R/D33E-GLP-2(1-33); D3E/D8K/K30R/D33E-GLP-2(1-33); D3E/E9K/K30R/D33E-GLP-2(1-33); D3E/M10K/K30R/D33E-GLP-2(1-33); D3E/N11K/K30R/D33E-GLP-2(1-33); D3E/T12K/K30R/D33E-GLP-2(1-33); D3E/I13K/K30R/D33E-GLP-2(1-33); D3E/L14K/K30R/D33E-GLP-2(1-33); D3E/D15K/K30R/D33E-GLP-2(1-33); D3E/N16K/K30R/D33E-GLP-2(1-33); D3E/L17K/K30R/D33E-GLP-2(1-33); D3E/A18K/K30R/D33E-GLP-2(1-33); D3E/D21K/K30R/D33E-GLP-2(1-33); D3E/N24K/K30R/D33E-GLP-2(1-33); D3E/Q28K/K30R/D33E-GLP-2(1-33); and precursors thereof.

29. The process according to claim 1, wherein said protein is exendin-3, exendin-4 or analogs thereof and precursors of any of the foregoing.

30. The process according to claim 29, wherein said protein is ZP-10 (HGEGTFTSDLSKQMEEEAVR-LFIEWLKNGGPSSGAPPSKKKKKK-NH2).

31. A process for purifying a fermentation-derived protein, said process comprising microfiltration of a fermentation broth containing the protein at a microflitration temperature within the range from 66° C. to 90° C. and wherein the protein is produced by a host cell selected from the group consisting of *E. coli, Saccharomyces, Pichia, Candida* and *Kluyveromyces*.

* * * * *